United States Patent [19]

Cvitas et al.

[11] Patent Number: 4,749,651

[45] Date of Patent: Jun. 7, 1988

[54] PROCESS FOR ENZYMATICALLY SACCHARIFYING STARCH-CONTAINING RAW-MATERIALS

[75] Inventors: Vilim Cvitas; Karl Faltejsek, both of Linz; Reinhart Hanke; Bertalan Treso, both of Leoben, all of Austria

[73] Assignee: Voest-Alpine Aktiengesellschaft, Vienna, Austria

[21] Appl. No.: 570,284

[22] Filed: Jan. 12, 1984

[30] Foreign Application Priority Data

Jan. 13, 1983 [AT] Austria ................................ 107/83

[51] Int. Cl.$^4$ .......................... C12P 19/14; C12P 7/14; C12N 1/16; C12N 1/18
[52] U.S. Cl. ...................................... 435/99; 435/162; 435/813; 435/255; 435/256
[58] Field of Search ..................... 435/93, 162, 96, 99, 435/813, 255, 256

[56] References Cited

U.S. PATENT DOCUMENTS 4,243,750  1/1981  Muller et al. ...................... 435/162
4,306,023 12/1981  Crombie ............................. 435/93

Primary Examiner—Lionel M. Shapiro
Attorney, Agent, or Firm—Cushman, Darby & Cushman

[57] ABSTRACT

In an enzymatic saccharification process, a sugar solution of constant sugar content is obtained by adding to the starch-containing raw materials, prior to the enzymatic saccharification step, part of the sugar solution obtained after the saccharification step and being separated from solid material and having been brought to a higher concentration, so that a higher sugar content, in particular within the range from 15 to 22% by weight and preferably approximately 20% by weight, can constantly be maintained, independent of the concentration and quality of the raw materials.

3 Claims, 1 Drawing Sheet

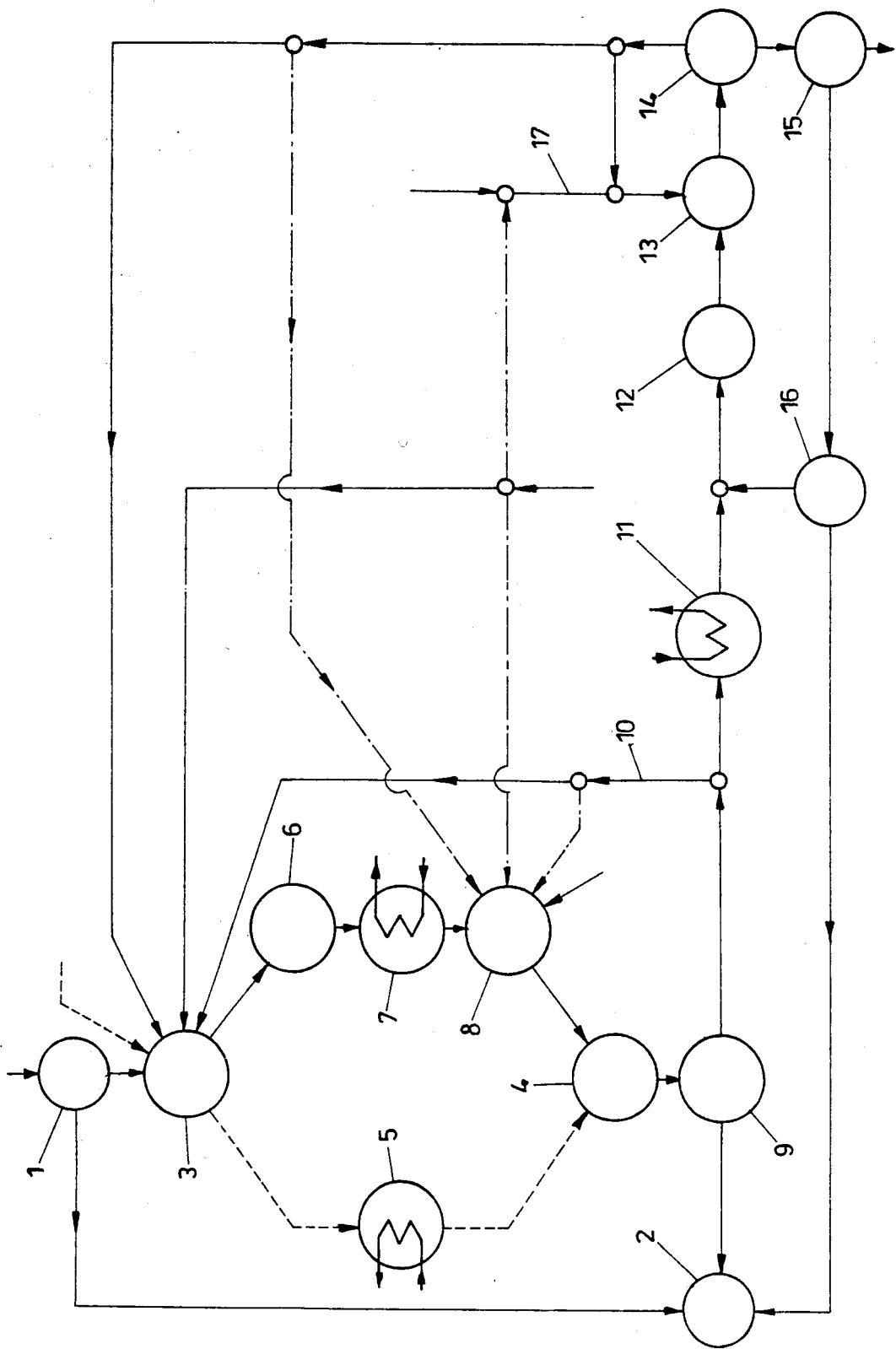

PROCESS FOR ENZYMATICALLY SACCHARIFYING STARCH-CONTAINING RAW-MATERIALS

The invention refers to a process for enzymatically saccharifying starch-containing raw materials. From EP-A No. 0 044 428 it is already known to produce, for the purpose of producing alcohol (ethanol), from starch or starch-containing raw materials, a mash which is informed by comminution, thermal degradation and saccharification of the starch-containing raw materials. There is known a plurality of sugar-containing raw materials from which sugar solutions can be obtained by an extraction process, and it is already known to degrade such sugar solutions down to glucose and to subject the mash thus obtained to fermentation. The fermentation process requires different process conditions depending on the raw materials and, respectively, the mash used, and requires a relatively long duration of reaction for completing the fermentation. It is a drawback of the known fermentation processes that the mashes or, respectively, fermentable substrates shown, during the fermentation reaction, differing concentrations of fermentable sugar as well as of fermentation products, which strongly influence the reaction speed and, respectively, the fermentation speed with increasing fermentation time. It is a further drawback of the known processes that always only a more or less pure alcohol can be produced, and this, as a rule, with only a low concentration.

The sugar-containing fermentation substrate which is obtained by a saccharification process shows—depending upon the yield in the saccharification process as well as depending upon the quality of the starch-containing raw material—differing concentrations of sugar, and these differing concentrations are particularly disadvantageous for rapid progress during the subsequent fermentation process. The sugar containing solutions throughout this specification and of the present invention are intended to include the numerous fermentable sugars normally produced by saccharification. The invention now aims at obtaining a fermentation substrate which ensures that the sugar concentration remains constant, independent of the yield of the saccharification step and of the quality of the starch-containing raw materials. For solving this task, the invention essentially consists in that the starch-containing raw materials are, prior to the saccharification step, mixed with part of the sugar solution obtained after the saccharification step and having been separated from solid matter and having been brought to a higher concentration, and in that the recycled portion of the sugar solution, which is recycled to the saccharification step, is selected in dependence on the starch content of the raw materials such that the sugar solution obtained after the saccharification step has a constant sugar content, in particular within the range of 15 to 22% by weight, preferably approximately 20% by weight.

By recycling part of the sugar solution obtained, the concentration can be controlled exactly. If the saccharification step is preceded by a gelatinization step or, respectively, a thermal conditioning step, this step is, as a rule, performed at temperatures of approximately 120° C. By adding the sugar solution, which has been separated from solid matter and has been brought to a higher concentration and which has of course become cooled, there is provided the possibility of simultaneously adjusting the temperatures of approximately 70° C. usually maintained in the saccharification stage and of simultaneously improving the energy balance. The process according to the invention is performed such that the proportion of the sugar solution recycled into the saccharification stage is selected in dependence on the starch content of the raw materials such that after the saccharification stage, a sugar solution is obtained having a constant sugar content, in particular within the range of 15 to 22% by weight, preferably approximately 20% by weight. Thus a fermentation substrate of constant sugar concentration is obtained, and simultaneously the energy balance is improved. By separating the solid material from the sugar solution to be recycled, there already results an increase in the concentration, which can of course be further increased by evaporation or, respectively, thickening.

It has surprisingly been found that in spite of increasing the sugar content at the very beginning of the saccharification step, the enzymes are not blocked, and that the enzymatic saccharification is not in the least adversely affected by the addition of a sugar-containing solution.

In the following, the invention is further illustrated with reference to an embodiment shown in the drawing.

In the process shown in the flow diagram, crude corn is mechanically processed in the first stage, designated by 1. The sieve overflow, which primarily contains the skins, is supplied to an animal feeding stuff production 2. The mechanically treated material is mixed with water at 3. If immediately subsequently the saccharification 4 takes place, the enzyme solution is simultaneously supplied and the solution is heated by a heating means 5 to a saccharification temperature of approximately 70° C. If prior to saccharification a thermal conditioning is to take place, no enzyme solution can be added prior to the thermal conditioning, because this solution would be destroyed at the higher temperatures of the thermal degradation. In this case, the mixture coming from 3 is heated to approximately 120° C. at 6 and thermally degraded and subsequently subjected to cooling 7 for adjusting the conditions for the saccharification stage. In this case, the enzyme solution is supplied to a mixing station 8 following the cooling stage. The saccharified solution is subjected to a separation step 9 and separated into a sugar solution freed of solid material and into a sludge cake, which sludge cake can again be supplied to the animal feeding stuff production 2. A portion of this sugar solution freed of solid material is recycled to the mixing stage 3 via a conduit 10. In case of a thermal conditioning stage, a portion of this sugar solution freed of solid matter can also be supplied to the second thermal mixing stage 8. The main portion of the sugar solution freed of solid matter is then cooled down to approximately 30° C. at 11 and, after an inoculation with yeast, supplied to a mixing stage 12. During mixing, flocculation can also be effected at 13 and flotation can be effected at 14, whereupon the yeast sludge rich in sugar is is subjected to fermentation at 15. After the fermentation is finished, the yeast can be supplied to a yeast recovery stage 16, noting that any excessive yeast is supplied to the animal feeding stuff production 2 and part of the recovered yeast is again added to the sugar solution freed of solid matter.

For the purpose of flocculation, a polyelectrolyte is supplied via a conduit 17 and, within the mixing stage 13, where the flocculation also takes place, residual water from the flotation can additionally be used. The residual water from the flotation is used together with fresh water within the mixing stage 3 and a respectively, the mixing stage 8.

The residual water from the flotation also contains fermentable sugar, and the fermentable sugar not yet subjected to fermentation is circulated as a whole. It is possible to control the sugar content of the sugar solution obtained at 4 after the saccharification step by means of the sugar solution freed of solid materials and extracted via the conduit 10, as well as by means of the residual water coming from the flotation.

What is claimed is:

1. A process for enzymatically saccharifying starch containing raw materials to produce a fermentable sugar solution to process comprising: subjecting said starch containing raw materials to enzymatic saccharification and recycling the produced fermentable sugar solution to the raw material in an amount whereby saccharification results in a fermentable sugar solution in the range of 15 to 22% by weight sugar, the process further including the step of concentrating the recycted fermentable sugar solution prior to addition to the raw materials.

2. A process of producing a fermentable sugar solution by enzymatic saccharification comprising subjecting a starch containing solution to a saccharification step to produce said fermentable sugar solution, concentrating a portion of the thus-produced sugar solution and recycling the resulting concentrate to the saccharification step in an amount whereby the fermentable sugar solution is produced with a constant sugar content of 15-22% by weight.

3. The process according to claim 2 wherein the concentrated sugar solution is recycled in an amount whereby the fermentable sugar solution has a sugar content of approximately 20%.

* * * * *